(12) United States Patent
Schilling

(10) Patent No.: US 10,024,773 B1
(45) Date of Patent: Jul. 17, 2018

(54) SYSTEM AND METHOD FOR LOADING A TEST ASSET

(71) Applicant: THE BOEING COMPANY, Chicago, IL (US)

(72) Inventor: Kenneth P. Schilling, West Chester, PA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/405,794

(22) Filed: Jan. 13, 2017

(51) Int. Cl.
*G01N 3/02* (2006.01)
*G01N 3/20* (2006.01)

(52) U.S. Cl.
CPC ................. *G01N 3/20* (2013.01); *G01N 3/02* (2013.01)

(58) Field of Classification Search
CPC .................................. G01N 3/20; G01N 3/02
USPC .................................................... 73/849, 853
See application file for complete search history.

(56) References Cited

U.S. PATENT DOCUMENTS

| | | | | |
|---|---|---|---|---|
| 4,166,377 A * | 9/1979 | Szabo | ................... | G01M 7/045 73/11.05 |
| 5,231,882 A * | 8/1993 | Bertele | ..................... | G01N 3/32 73/852 |
| 8,544,340 B1 * | 10/2013 | Ardelean | ................. | G01N 3/20 73/849 |
| 8,863,585 B2 * | 10/2014 | Wang | ....................... | G01N 3/34 73/812 |
| 9,091,619 B2 * | 7/2015 | Gregg | ....................... | G01N 3/24 |
| 9,605,993 B2 * | 3/2017 | Ziebart | ................ | G01G 3/1408 |
| 2013/0205911 A1 * | 8/2013 | Wang | ....................... | G01N 3/34 73/812 |
| 2015/0040680 A1 * | 2/2015 | Gregg | ....................... | G01N 3/24 73/842 |
| 2015/0308883 A1 * | 10/2015 | Ziebart | ................ | G01G 3/1408 177/132 |

FOREIGN PATENT DOCUMENTS

JP 2011257355 A 12/2011
WO 2016149135 A1 9/2016

OTHER PUBLICATIONS

"Lightweight Concrete: Development of Mild Steel in Tension," Federal Highway Administration, Publication No. FHWA-HRT-14-030, Feb. 2014; https://www.fhwa.dot.gov/publications/research/infrastructure/structures/bridge/14030/index.cfm, 14 pgs.
Extended European Search Report dated Apr. 25, 2018 for Application No. 17199262.1, 9 pgs.

* cited by examiner

*Primary Examiner* — Jonathan Dunlap
(74) *Attorney, Agent, or Firm* — Toler Law Group, PC

(57) ABSTRACT

A test structure includes a frame, a shear reduction plate configured to couple to a first end of a test asset, and multiple rockers. Each rocker includes a first end that has a curved contact surface configured to contact the shear reduction plate and a second end having a connector movably coupled to the frame and configured to pivot, responsive to a bending moment applied to the test asset, such that the curved contact surface rocks in contact with the shear reduction plate.

20 Claims, 6 Drawing Sheets

600

602
APPLY AN AXIAL LOAD TO A TEST ASSET IN A TEST STRUCTURE, THE TEST STRUCTURE INCLUDING A FRAME, A SHEAR REDUCTION PLATE COUPLED TO A FIRST END OF A TEST ASSET, MULTIPLE ROCKERS, EACH ROCKER INCLUDING A FIRST END AND A SECOND END, THE FIRST END HAVING A CURVED CONTACT SURFACE CONFIGURED TO CONTACT THE SHEAR REDUCTION PLATE, THE SECOND END HAVING A CONNECTOR MOVABLY COUPLED TO THE FRAME AND CONFIGURED TO PIVOT, RESPONSIVE TO A BENDING MOMENT APPLIED ON THE TEST ASSET, SUCH THAT THE CURVED CONTACT SURFACE ROCKS IN CONTACT WITH THE SHEAR REDUCTION PLATE

604
APPLY A TRANSLATIONAL LOAD TO THE TEST ASSET, THE TRANSLATIONAL LOAD ORTHOGONAL TO THE AXIAL LOAD, WHEREIN THE TRANSLATIONAL LOAD CAUSES THE BENDING MOMENT

SYSTEM AND METHOD FOR LOADING A TEST ASSET

GOVERNMENT LICENSE RIGHTS

This invention was made with Government support under NNM07AB03C awarded by NASA. The Government has certain rights in this invention.

FIELD OF THE DISCLOSURE

The present disclosure is generally related loading a test asset to experience a bending moment.

BACKGROUND

Beam reaction systems and test loading systems apply loads (e.g., forces) to a test asset (e.g., a beam or a portion thereof) to simulate operational loads. When applying a uniform bending moment to a test asset (or a portion thereof), rollers or spherical balls are utilized to simulate theoretical constraints for applying the uniform bending moment when a translational load (e.g., a transverse load) is applied. As an axial load applied to the test asset increases, so does a size (e.g., a diameter) of the rollers or spherical balls, an amount of the rollers or spherical balls, or a combination there of, used to satisfy Hertzian contract stress constraints. In order to test large axial loads, large spherical balls or a large number of smaller spherical balls are used to satisfy the Hertzian contract stress constraints. Use of such large spherical balls or large numbers of smaller spherical balls is impractical and cost-prohibitive.

SUMMARY

In a particular implementation, a test structure includes a frame, a shear reduction plate configured to couple to a first end of a test asset, and multiple rockers. Each rocker includes a first end that has a curved contact surface configured to contact the shear reduction plate and a second end having a connector movably coupled to the frame and configured to pivot, responsive to a bending moment applied to the test asset, such that the curved contact surface rocks in contact with the shear reduction plate.

In another particular implementation, a test structure includes a frame, a shear reduction plate configured to couple to a first end of a test asset, and multiple rockers. Each rocker includes a first end that has a curved contact surface configured to contact the shear reduction plate and a second end having a connector movably coupled to the frame. The multiple rockers include a first set of rockers on a first side the shear reduction plate and a second set of rockers on a second side of the shear reduction plate. Each rocker of the second set of rockers is aligned, through the shear reduction plate, with a corresponding rocker of the first set of rockers.

In another particular implementation, a method of applying a uniform bending moment includes applying an axial load to a test asset in a test structure, where the test structure includes a frame, a shear reduction plate configured to couple to a first end of a test asset, and multiple rockers. Each rocker includes a first end that has a curved contact surface configured to contact the shear reduction plate and a second end having a connector movably coupled to the frame and configured to pivot, responsive to a bending moment applied to the test asset, such that the curved contact surface rocks in contact with the shear reduction plate. The method also includes applying a translational load to the test asset. The translational load is orthogonal to the axial load and causes the bending moment.

BRIEF DESCRIPTION OF THE DRAWINGS

FIG. 6 is a flow chart of an example of a method for loading a test asset.

DETAILED DESCRIPTION

Implementations disclosed herein are directed to systems for loading a test asset. An exemplary system for loading a test asset includes a frame, a test asset, a shear reduction plate, and multiple rockers. The test asset is coupled to the frame and to the shear reduction plate. The multiple rockers are moveably coupled to the frame and contact the shear reduction plate. To illustrate, each rocker includes a first end that has a curved contact surface configured to contact the shear reduction plate and a second end having a connector movably coupled to the frame and configured to pivot, responsive to one or more loads applied to the test asset, such that the curved contact surface rocks in contact with the shear reduction plate.

The system also includes an axial loader configured to apply an axial load to the test asset and a translational loader configured to apply a translational load (e.g., transverse load) to the test asset. Application of the axial load and the translational load causes the test asset (or a portion thereof) to experience a uniform bending moment.

The rockers simulate the movement of rollers or spherical balls to satisfy Hertzian contact stress constraints. By using rockers instead of large rollers or large spherical balls, the system is smaller and has reduced material costs. For example, a system with rockers is smaller than a system with rollers or spherical balls that have the same curvature as the rockers. Additionally, by using rockers, instead of smaller rollers or smaller spherical balls, the system can be less complex since a total number of components used can be reduced.

Figure 1:
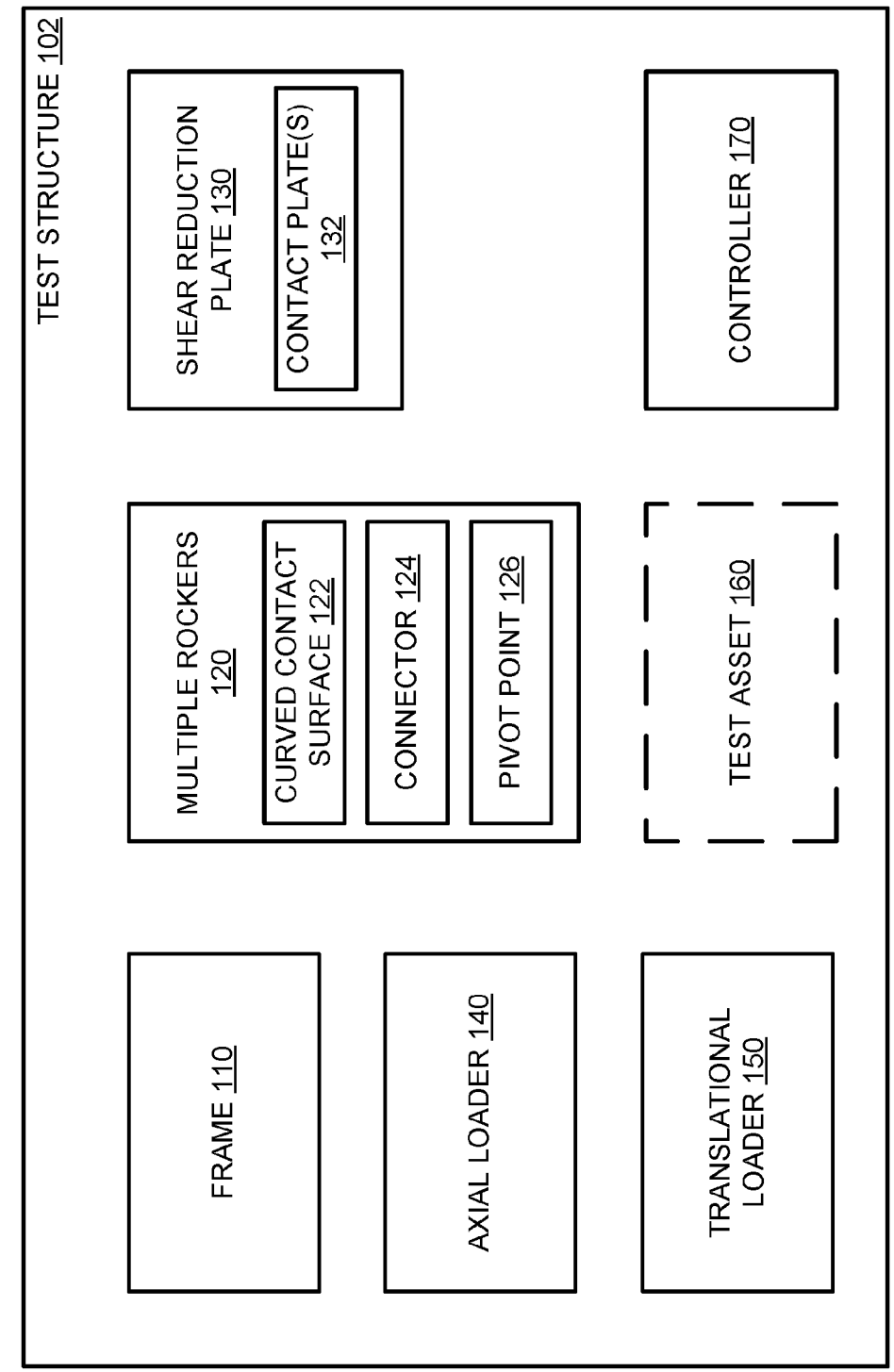
FIG. 1 is a block diagram that illustrates an example of a system for loading a test asset.

FIG. 1 illustrates an example of a system 100 for loading a test asset 160. The system 100 may enable applying a uniform bending moment to the test asset 160. The system 100 includes a test structure 102 that includes a frame 110, multiple rockers 120, a shear reduction plate 130, an axial loader 140, and a translational loader 150 (e.g., a transverse loader). The test structure 102 is capable of housing the test asset 160 and applying loads to perform one or more tests on the test asset 160, such as a structural failure analysis test.

The frame 110 is configured to support the test structure 102 and the components thereof. For example, the frame 110 may be coupled to the multiple rockers 120, the shear reduction plate, 130, the axial loader 140, and the translational loader 150. In other implementations, the axial loader 140 and the translational loader 150 are separate from the frame 110. The frame 110 is configured to be coupled to the test asset 160 (e.g., a second end of the test asset 160). In some implementations, the frame 110 (or brackets thereof) are adjustable to accommodate different sized components (e.g., rockers).

The multiple rockers 120 are movably coupled to the frame 110 such that the multiple rockers 120 can move in multiple directions. Each rocker includes a first end that includes a curved contact surface 122 and a second end that includes a connector 124 and a pivot point 126. The curved contact surface 122 is configured to contact the shear reduction plate 130 (or a contact plate 132 thereof) and to move in contact with the shear reduction plate 130. For example, the curved contact surface 122 of a particular rocker of the multiple rockers 120 is configured to rock or pivot to align an axial load along the particular rocker. In some implementations, the curved contact surface 122 includes a section of a sphere. For example, the curved contact surface 122 is curved in two orthogonal planes. In some implementations, a curvature of the curved contact surface 122 (e.g., the section of the sphere) of each rocker is the same. The curvature of the curved contact surface 122 is proportional to an axial load applied to the test asset 160 (and to a number of rockers of the multiple rockers 120).

The connector 124 and the pivot point 126 are configured to enable movement of the multiple rockers 120 in the multiple directions. The connector 124 of a particular rocker is configured to pivot, about the pivot point 126, in two orthogonal planes as the curved contact surface 122 of the particular rocker rocks in the two orthogonal planes. The connector 124 may include or correspond to a rod end that includes a rod eye. The pivot point 126 may include or correspond to a spherical bearing (e.g., a spherical plain bearing or a spherical roller bearing). In such implementations, the spherical bearing may be positioned in the rod eye.

In some implementations, the connector 124 of each rocker is movably coupled to a corresponding bracket mounted to the frame 110. In a particular implementation, the connector 124 of each rocker is movably coupled to a corresponding clevis bracket via a clevis pin. In such implementations, the clevis pin may include or correspond to a spherical bearing.

A distance from the pivot point 126 to the curved contact surface 122 of a particular rocker is proportional to an axial load to be applied to the test asset 160 (and proportional to a number of rockers of the multiple rockers 120). For example, as an axial load increases, the distance increases. The distance may correspond to a radius of a sphere that is associated with the curvature of the curved contact surface 122.

The shear reduction plate 130 may be coupled to the frame 110 via the multiple rockers 120 and may be movable with respect to the frame 110. The shear reduction plate 130 is configured to contact the multiple rockers 120 and is configured to move (e.g., translate) responsive to movement of the multiple rockers 120. For example, because of rocking of the curved contact surface 122 of one or more rockers of the multiple rockers 120, the shear reduction plate 130 applies zero (or negligible) shear force and a uniform bending moment on the test asset 160.

In some implementations, the shear reduction plate 130 includes multiple contact plates 132. The curved contact surface 122 of each rocker is configured to move (e.g., rock) in contact with a corresponding contact plate of the multiple contact plates 132. The contact plates 132 include a second material with a greater hardness than a first material of the shear reduction plate 130. In a particular implementation, the second material includes hardened steel. Additionally or alternatively, the second material may have a greater stiffness than the first material of the shear reduction plate 130. In some implementations, the curved contact surface 122 also includes the second material, such as hardened steel.

The axial loader 140 is coupled to the frame 110 and configured to apply an axial load to the test asset 160. The translation loader 150 is coupled to the frame 110 and configured to apply a translational load (e.g., transverse load) and the uniform bending moment to the test asset 160. The translational load is orthogonal to the axial load and causes the test asset 160 to experience the uniform bending moment. The axial load and the translational load are applied at or near the second end of the test asset 160.

The test asset 160 is coupleable to the shear reduction plate 130 and the frame 110. The test asset 160 includes or corresponds to a structural element that is configured to withstand a load. The test asset 160 may withstand the load by resisting deflection, bending, or other deformation. In a particular implementation, the test asset 160 may include or correspond to a beam that is configured to withstand an axial load and a translational load. The loads may cause the test asset 160 (or a portion thereof) to experience a uniform bending moment.

In some implementations, the system 100 includes a controller 170 configured to control and operate application of the loads and testing of the test asset 160. The controller 170 may be part of or separate from the test structure 102. The controller 170 sends control signals to the axial loader 140, the translational loader 150, or both, to initiate application of the loads or to adjust the load. In some implementations, the controller 170 is configured to determine an amount of the load (e.g., a magnitude of the load) based on the bending moment, the curvature of the curved contact surface 122, the distance from pivot point 126 to curved contact surface 122, the number of rockers of the multiple rockers 120, or a combination thereof. For example, the controller 170 may use Hertzian contact stress equations to calculate the axial load. Additionally or alternatively, the controller 170 is configured to determine the curvature of the curved contact surface 122, the distance from pivot point 126 to curved contact surface 122, or both, based on the axial load, the bending moment, the number of rockers, or a combination thereof. In a particular implementation, a position of the multiple rockers 120 may be adjustable. In such implementations, the controller 170 may be configured to adjust a position of particular rocker with respect to the shear reduction plate 130. To illustrate, the controller 170 may send signals to adjust a spacing between the multiple rockers 120 (the pivot point 126 thereof) and the shear reduction plate 130.

During operation, a first end of the test asset 160 is coupled to the shear reduction plate 130 and a second end of the test asset 160 is coupled to the axial loader 140 and to the translational loader 150. The controller 170 may initiate application of the axial load by the axial loader 140, initiate application of the translational load by the translational loader 150, or both, to the test asset 160. During application of the loads, the test asset 160 experiences a bending moment, such as a uniform bending moment further described with reference to FIG. 2. To illustrate, the shear reduction plate 130 may translate in a direction parallel to the translational load and orthogonal to the axial load. As the shear reduction plate 130 translates, the curved contact surface 122 of each rocker of the multiple rockers 120 moves (e.g., swings, pivots, or rocks) such that the curved contact surface 122 remains in contact with the shear reduction plate 130 (or a corresponding contact plate 132 thereof).

The multiple rockers 120 and the shear reduction plate 130 provide a reaction force that opposes the axial force. The multiple rockers 120 and shear reduction plate 130 provide less than a threshold force (or no force) that opposes the translational force such that the test asset 160 experience negligible shear force at the first end.

In some implementations, the system 100 may include one or more springs coupled to the frame 110 and to one or more rockers of the multiple rockers 120. The one or more springs are configured to bias the one or more rockers such that a center of the curved contact surface 122 of the one or more rockers is in contact with the shear reduction plate 130 as further described with reference to FIG. 5. By using rockers the system may be smaller and have reduced costs as compared to systems that utilize rollers or spherical balls. Additionally, by using rockers the test asset 160 may experience a uniform bending moment while larger axial forces are being applied to the test asset 160.

Figure 2:
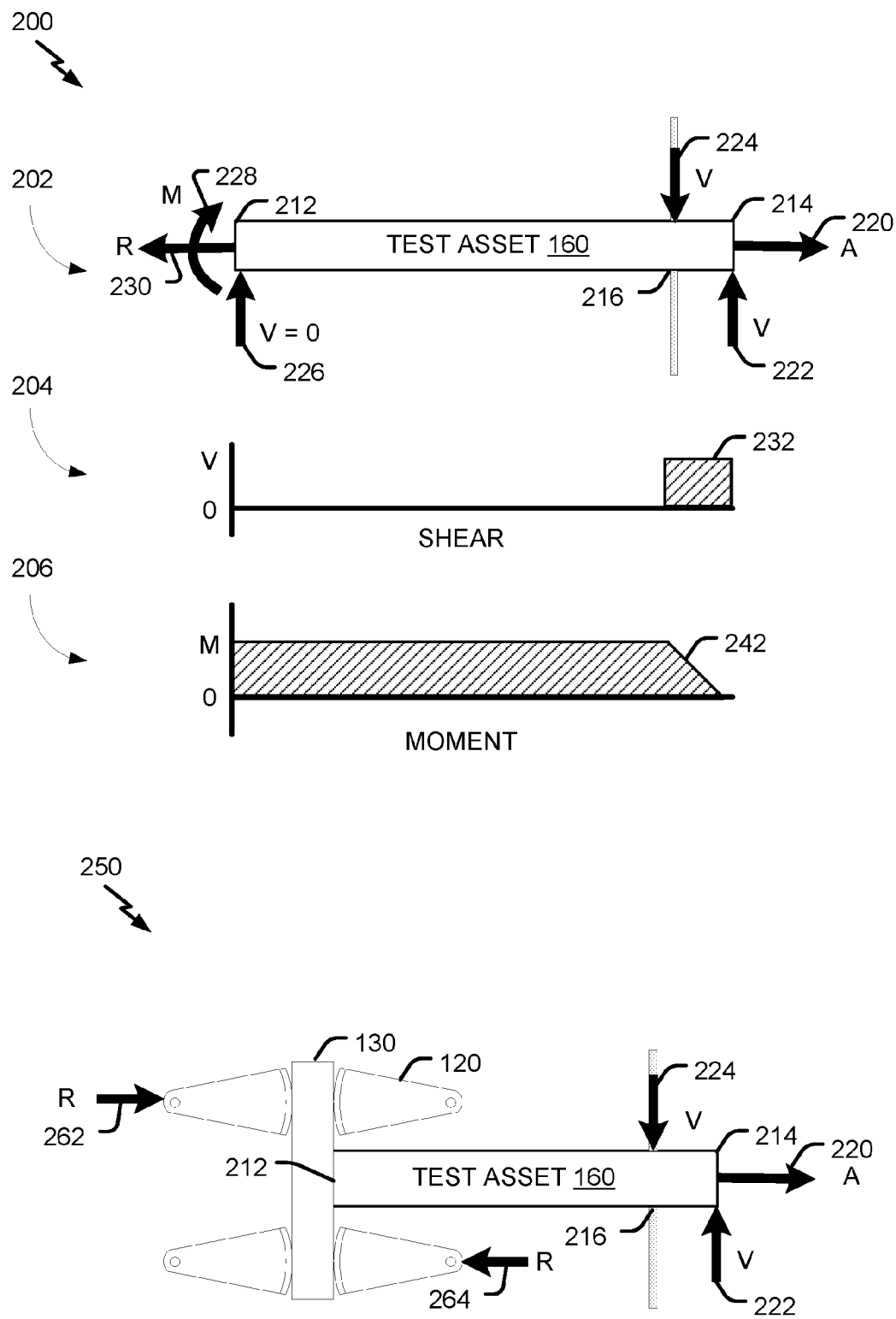
FIG. 2 is a diagram that illustrates loading diagrams of a test asset.

FIG. 2 illustrates loading diagrams 200 of the test asset and a two-dimensional diagram of a loading configuration 250 of an example of the system 100. In FIG. 2, "A" denotes an axial load or force, "V" denotes a shear force, "M" denotes a moment, "R" denotes a reaction force, and arrows designate a direction of the load, force, or moment.

The loading diagrams 200 include a test loading diagram 202, a shear diagram 204, and a bending moment diagram 206. The test loading diagram 202 illustrates an exemplary test loading of the test asset 160. As illustrated in the test loading diagram 202 of FIG. 2, the test asset 160 includes a first end 212 and a second end 214. The test asset 160 is supported by a support at a support point 216 between the first end 212 and the second end 214. The support point 216 may include or correspond to pin support or a roller support. An axial load 220 is applied to the second end 214 of the test asset 160 and a shear force 222 (e.g., a translational or transverse load) is applied to the test asset 160 at or near the second end 214. The support applies a shear force 224 at the support point 216. A direction of the shear force 224 is opposite that of the shear force 222, and the shear forces 222, 224 have the same magnitude. A moment 228 and an axial reaction force 230 are applied to the first end 212 of the test asset 160 by a support (not shown), such as the shear reduction plate 130. A direction of the axial reaction force 230 is opposite that of the axial load 220, and the axial load 220 and the axial reaction force 230 have the same magnitude. Accordingly, the test asset 160 experiences no (or negligible) shear force 226 at or near the first end 212. The shear forces 224 and 226 may correspond to reactionary shear forces. The axial load 220, the shear force 222, and the moment 228 may cause the test asset 160 to experience a uniform bending moment.

Responsive to the loads and forces applied, the test asset 160 experiences shear and moments as illustrated in the diagrams 204, 206. Referring to the shear diagram 204, the test asset 160 experiences negligible shear force (or less than a threshold amount of shear force) at the first end 212 and experiences a shear force 232 of magnitude V at and near the second end 214. The magnitude V corresponds to the magnitude of the shear forces 222, 224. The test asset 160 experiences the shear force 232 from the support point 216 to the second end 214. Referring to the bending moment diagram 206, the test asset 160 experiences a positive bending moment 242 (e.g., clock-wise as illustrated in FIG. 2) that is greater at the first end 212 than the second end 214. A magnitude M of the positive bending moment 242 is constant for a majority of the beam, from the first end 212 to the support point 216, as illustrated in FIG. 2. Thus, the test asset 160 experiences a uniform bending moment between the first end 212 and the support point 216. A uniform bending moment (e.g., a constant bending moment) exerts no shear force on the test asset 160, and the test asset 160 may deflect (e.g., bend) in an arc such that every element of the beam between the first end and the support point 216 is deflected the same amount (e.g., with the same radius of curvature).

Referring to the loading configuration diagram 250, an exemplary test asset loading configuration that corresponds to the loading diagrams 200 is illustrated. As illustrated in the loading configuration diagram 250 of FIG. 2, the first end 212 of the test asset 160 is coupled to the shear reduction plate 130, and the multiple rockers 120 are in contact with the shear reduction plate 130. The configuration illustrated in the loading configuration diagram 250 is configured to apply the uniform bending moment to the test asset 160. The test asset 160 experiences the shear forces as illustrated in the shear diagram 204 and the bending moment as illustrated in the bending moment diagram 206. To illustrate, the test asset 160 experiences reaction forces 262, 264 from the multiple rockers 120 which counteract the axial load 220 and gravity (e.g., a gravitational force). Displacement of the shear reduction plate 130 is guided by rocking of the multiple rockers 120 and allows bending of the test asset 160 without introducing shear forces. In some implementations, a first magnitude of the reaction force 262 is different from a second magnitude of the second reaction force 264.

Figure 3:
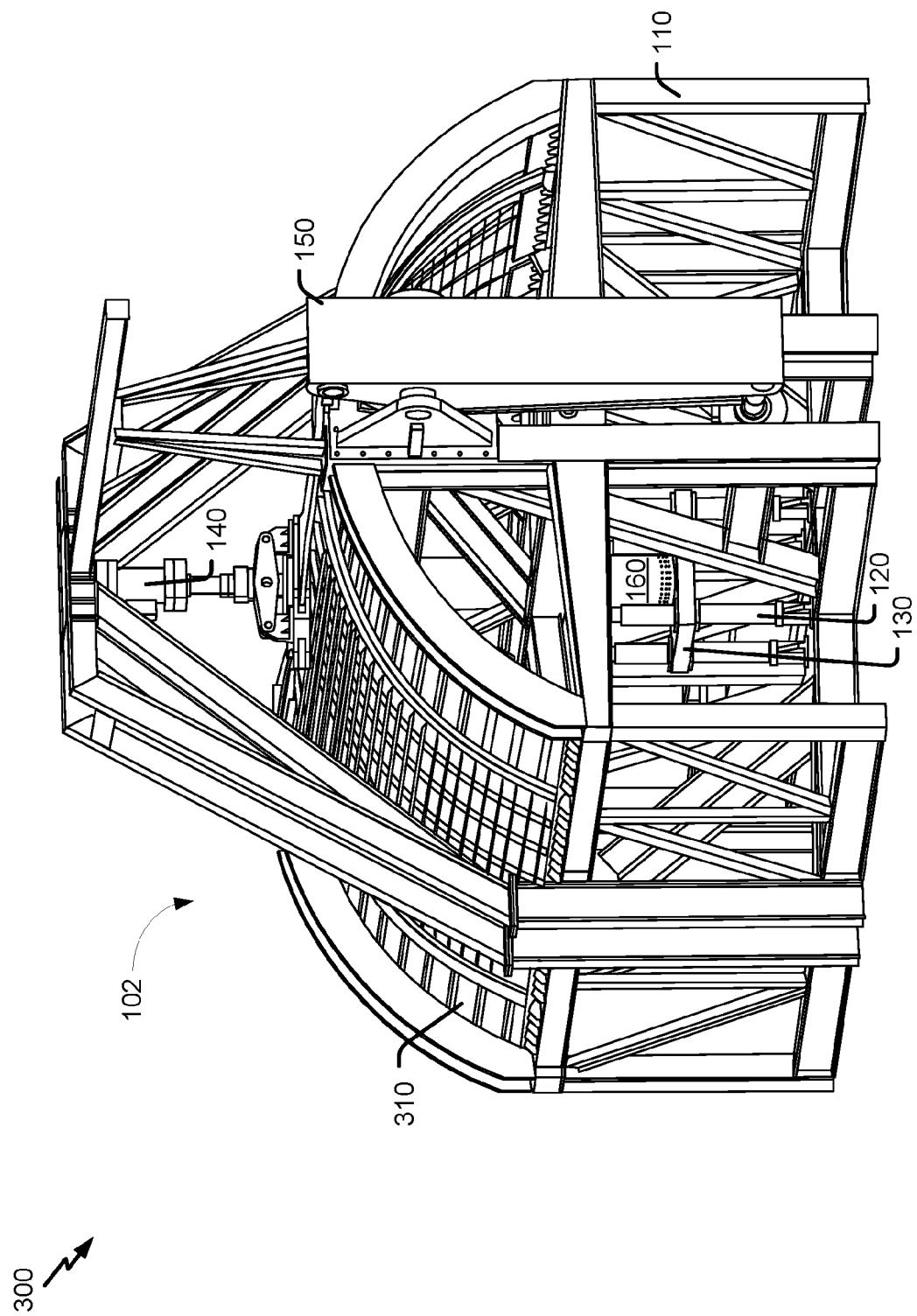
FIG. 3 is a diagram that illustrates an isometric view of an example of a system for loading a test asset.

FIG. 3 illustrates a diagram 300 of a particular example configuration of the test structure 102. As illustrated in FIG. 3, the test asset 160 is a beam with a circular cross section. In other implementations, the test asset 160 may include or correspond to other structural members having different shape cross sections. In a particular implementation, the test asset 160 corresponds to a thrust beam or a portion thereof.

As illustrated in FIG. 3, the axial loader 140 includes an actuator and generates the axial load which pulls the test asset 160 upwards (as illustrated in FIG. 3) to generate a tensile axial force. In other implementations, the axial loader 140 may generate a compressive axial force. The translational loader 150 includes an actuator and lever to generate and transfer the translational load to the test asset 160.

The test structure 102 may include a test asset frame 310 coupled to the second end of the test asset 160 and the frame 110 as illustrated in FIG. 3. The test asset frame 310 may include or correspond to a portion of an aircraft or a rocket. As illustrative, non-limiting examples, the test asset frame 310 corresponds to a sidewall of a rocket or a rocket booster.

As illustrated in FIG. 3, the multiple rockers 120 include a first set of rockers that includes four rockers and a second set of rockers that includes four rockers. The connector 124 of each rocker of the multiple rockers 120 is configured to pivot in two orthogonal planes, responsive to a load applied to the test asset 160, such that the curved contact surface 122 of each rocker rocks in contact with the shear reduction plate 130. The first set of rockers and second set of rockers are described further with reference to FIGS. 4 and 5.

Although the first set and the second set of rockers are illustrated as having four rockers each, in other implementations the first set and the second set of rockers may each have more than four rockers or fewer than four rockers (e.g., three rockers). Increasing a number of rockers decreases a distance from the pivot point 126 to the curved contact surface 122 (e.g., the radius) and increases a curvature of the curved contact surface 122 to satisfy Hertzian contact stress constraints. Also, increasing the number of rockers may decrease testing accuracy as variations between of components (e.g., rockers, contact plates) may increase because there are more components.

Figure 4:
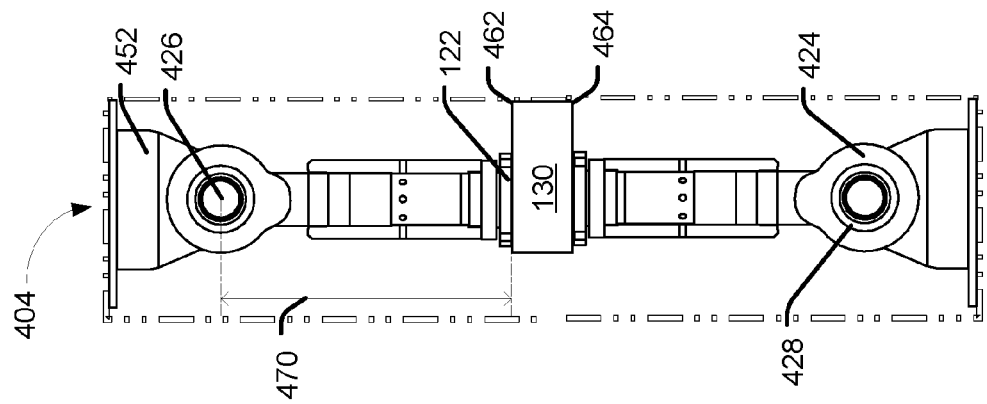
FIG. 4 is a detailed diagram of an example configuration of rockers of a system for loading a test asset.
Figure 4:
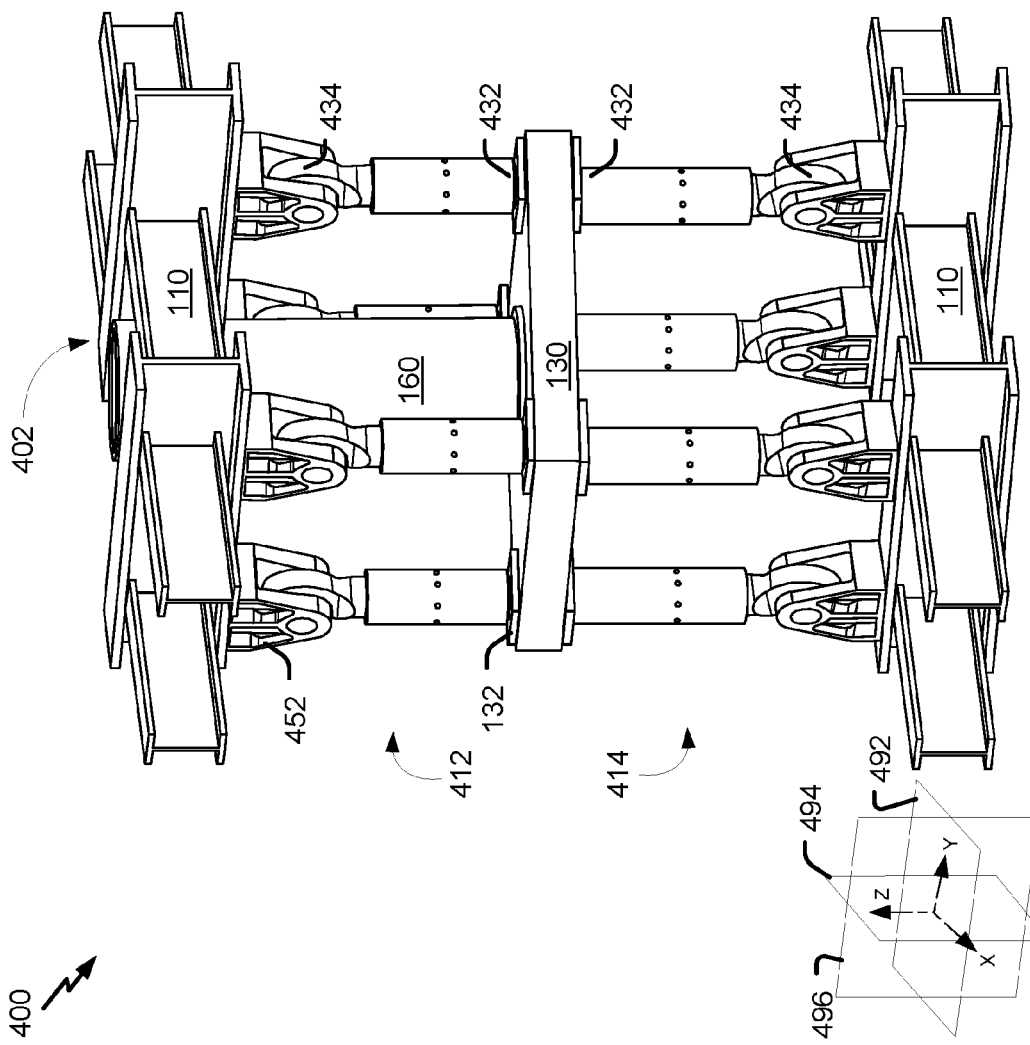

FIG. 4 illustrates an example 400 of detailed views of the example configuration of the multiple rockers 120 as illustrated in FIG. 3. A first diagram 402 illustrates a first set of rockers 412 positioned on a first side 462 of the shear reduction plate 130 and a second set of rockers 414 positioned on a second side 464 of the shear reduction plate 130. Each rocker of the second set of rockers 414 is aligned, through the shear reduction plate 130, with a corresponding rocker of the first set of rockers 412. Each rocker has a first end 432 that includes the curved contact surface 122 and a second end 434 that is movably coupled to a corresponding bracket 452 coupled to the frame 110. The first diagram 402 illustrates three orthogonal planes 492, 494, 496. Each rocker is configured to rock along two orthogonal planes such as the orthogonal planes 494, 496.

A second diagram 404 illustrates a pair of aligned rockers of the first and second sets of rockers 412, 414. For example, the pair of aligned rockers may have aligned pivot points and may rock in the same two orthogonal planes. Referring to the second diagram 404, the second end 434 of the rockers corresponds to a spherical rod end 424 with a spherical rod eye 428 as illustrated in FIG. 4. In a particular implementation, the spherical rod eye 428 includes a spherical bearing 426. The spherical bearing 426 may enable angular rotation of the rockers 412, 414 about a pivot point in two orthogonal directions. Movement of the rockers 412, 414 and the shear reduction plate 130 is described further with reference to FIG. 5. A distance 470 is illustrated from a pivot point (e.g., a center of the spherical bearing 426) to the curved contact surface 122 (e.g., any point on the curved contact surface). The distance 470 may correspond to a radius of a sphere that is associated with curvature of the curved contact surface 122. The distance 470 may also correspond to a distance between the pivot point (e.g., the center of the spherical bearing 426) and the shear reduction plate 130 (e.g., the contact plate 132 of the shear reduction plate 130). In the second diagram 404, a front portion of the bracket 452 has been omitted for clarity.

As illustrated in the first diagram 402 of FIG. 4, the contact plates 132 of the shear reduction plate 130 are raised or extend from a surface of the shear reduction plate 130. In other implementations, the contacts plates 132 of the shear reduction plate 130 may be flush with other surfaces of the shear reduction plate 130, as illustrated in the second diagram 404 of FIG. 4.

Figure 5:
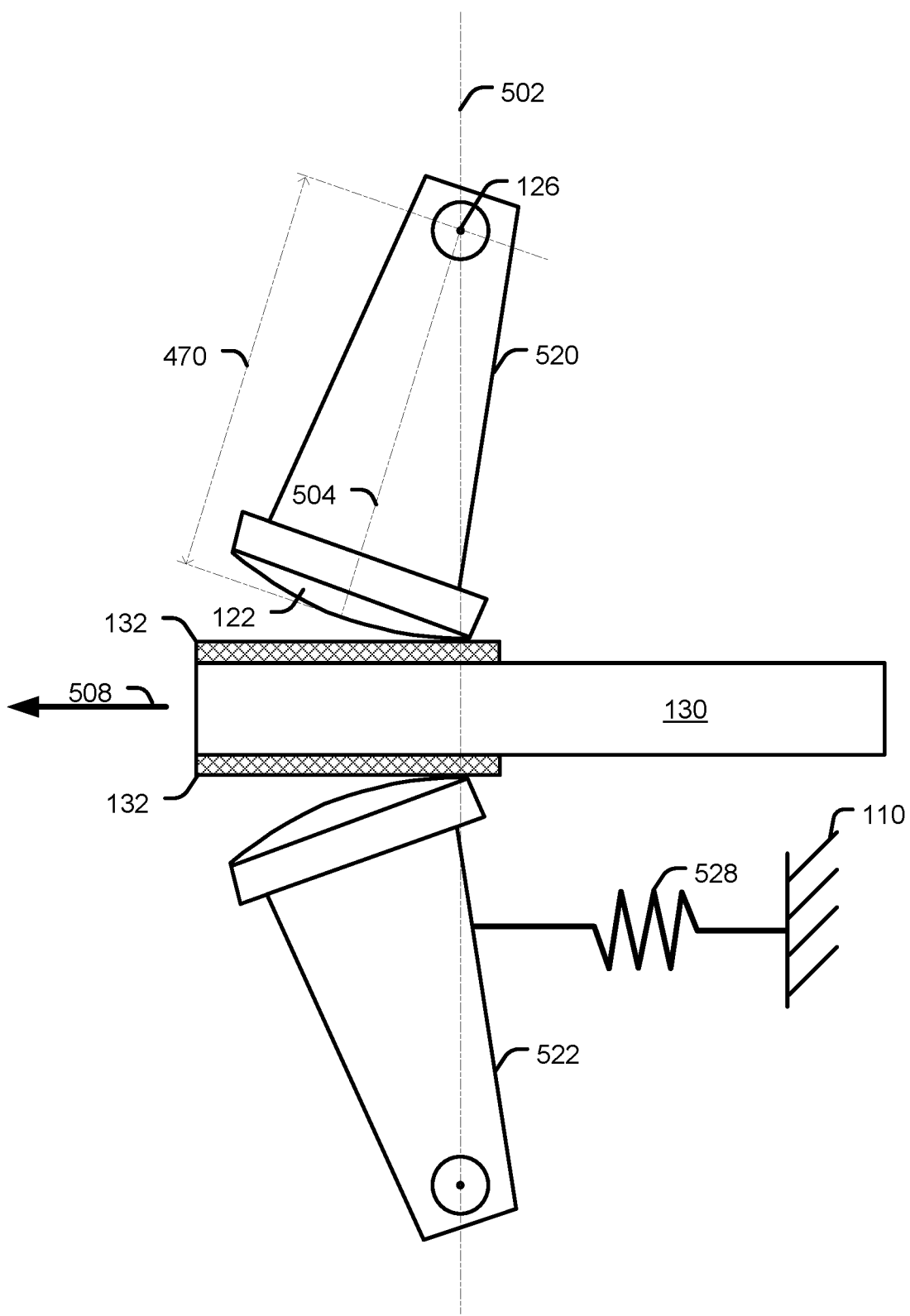
FIG. 5 is a diagram that illustrates movement of rockers of a system for loading a test asset.

FIG. 5 illustrates a two-dimensional diagram 500 of translation of a pair of aligned rockers of the multiple rockers 120 of FIG. 3 and the shear reduction plate 130. A first rocker 520 of the particular pair of aligned rockers corresponds to a first set of rockers, such as the first set of rockers 412 of FIG. 4, and a second rocker 522 of the particular pair of aligned rockers corresponds to a second set of rockers, such as the second set of rockers 414 of FIG. 4. As illustrated in FIG. 5, the pivot point 126 of each of the rockers 520, 522 is aligned by an axis 502. The axis 502 represents a starting position or untranslated position. An axis 504 represents a translated position. As the rockers 520, 522 translate from the starting position to the translated position illustrated in FIG. 5, the curved contact surface 122 rocks in contact with a corresponding contact plate 132. The shear reduction plate 130 translates in a direction 508 (leftward as illustrated in FIG. 5) responsive to application of a translational load. The shear reduction plate 130 can also translate in other directions responsive to the translational load or other loads. FIG. 5 also illustrates the distance 470 (e.g., a radius of the rocker 520) from the pivot point 126 to each point on the curved contact surface 122.

In some implementations, one or more springs 528 are coupled to the frame 110 and to one or more rockers of the multiple rockers. For example, the one or more springs may be coupled to one or more rockers of the second set rockers, such as the second rocker 522. The one or more springs 528 are configured to bias the one or more rockers such that a center of the curved contact surface of the one or more rockers is in contact with the shear reduction plate 130. To illustrate, a particular spring may bias a particular rocker in the starting position (e.g. an upright position) to counteract or reduce an influence of gravity (e.g., a gravitational force exerted on the particular rocker as the particular rocker swings away from the starting position). The particular spring may bias the particular rocker towards the starting position as the particular rocker pivots away from the starting position (e.g., the upright position). Additionally or alternatively, one or more springs may be coupled to one or more rockers of the first set rockers. In some implementations, each rocker may be coupled to multiple springs.

FIG. 6 illustrates a method 600 of applying a uniform bending moment. The method 600 may be performed by the system 100 of FIG. 1 or the controller 170 of FIG. 1. The method 600 includes, at 602, applying an axial load to a test asset in a test structure. The test structure includes a frame, a shear reduction plate configured to couple to a first end of a test asset, and multiple rockers. Each rocker includes a first end that has a curved contact surface configured to contact the shear reduction plate and a second end having a connector movably coupled to the frame and configured to pivot, responsive to a bending moment applied to the test asset, such that the curved contact surface rocks in contact with the shear reduction plate.

The axial load may include or correspond to the axial load 220 of FIG. 2. The axial load is applied by an axial loader, such as the axial loader 140 of FIG. 1. The test asset may include or correspond to the test asset 160 of FIG. 1, and the test structure may include or correspond to the test structure 102 of FIG. 1. The frame may include or correspond to the frame 110 of FIG. 1, and the shear reduction plate may include or correspond to the shear reduction plate 130 of FIG. 1.

The multiple rockers may include or correspond to the multiple rockers 120 of FIG. 1. The first end and the second end of the rockers may include or correspond to the first end 432 and the second end 434 of FIG. 4, respectively. The curved contact surface may include or correspond to the curved contact surface 122 of FIG. 1. The connector may include or correspond to the connector 124 of FIG. 1. In some implementations, the connector includes a pivot, such as the pivot point 126 of FIG. 1.

The method 600 of FIG. 6 further includes, at 604, applying a translational load to the test asset, the translational load orthogonal to the axial load, wherein the translational load causes the bending moment. As described above, application of the translational load to the test asset 160 causes the uniform bending moment, such as the moment 228 of FIG. 2. For example, the multiple rockers rock in contact with the shear reduction plate and guide translation of the shear reduction plate to cause the test asset 160 to experience a uniform bending moment responsive to application of the translational load. The multiple rockers 120 are configured to simulate rolling of rollers or spherical balls. Application of the axial load and the translational load may be associated with a structural failure analysis test. In some examples, the test asset may include or correspond to a thrust beam.

The translational load may include or correspond to the shear force 222 of FIG. 2. The translational load is applied by a translational loader, such as the translational loader 150 of FIG. 1. In some implementations, the multiple rockers and the shear reduction plate apply less than a threshold shear force, such as the shear force 226 of FIG. 2, to the test asset responsive to application of the translational load.

The method 600 may further include installing the test asset in a test structure or system prior to applying the axial load. For example, the test asset 160 may be coupled to the shear reduction plate 130, the axial loader 140, and the translational loader 150. After completion of a test, the test asset may be removed. Additionally, after completion of the test, such as a structure failure analysis test, a second test asset may be installed in the test structure or system. The second test asset may be similar to or different from the test asset. The method 600 may further include adjusting one or more of the axial load or the translational load. For example, the controller 170 of FIG. 1 may adjust the axial load, the translation load, or both, based on a desired loading scheme. Rockers and the frame may be adjusted based on the adjusted load. For example, when an axial load is increased, a distance between the pivot point and the curved contact surface is increased and a curvature of the curved contact surface is reduced. A first type (e.g., first length) rocker may be replaced by a second type (e.g., second length) rocker or a length of the rockers may be adjustable. A length of an adjustable rocker may be adjusted by the controller (e.g., activating an actuator in the adjustable rocker) or manually (e.g., adjusting placement of a pin). In such implementations, the curved contact surface of the adjustable rocker may be replaced with a second curved contact surface that corresponds to the length of the adjusted rocker. The frame or brackets thereof may be adjusted to accommodate the different sized rockers.

The illustrations of the examples described herein are intended to provide a general understanding of the structure of the various implementations. The illustrations are not intended to serve as a complete description of all of the elements and features of apparatus and systems that utilize the structures or methods described herein. Many other implementations may be apparent to those of skill in the art upon reviewing the disclosure. Other implementations may be utilized and derived from the disclosure, such that structural and logical substitutions and changes may be made without departing from the scope of the disclosure. For example, method operations may be performed in a different order than shown in the figures or one or more method operations may be omitted. Accordingly, the disclosure and the figures are to be regarded as illustrative rather than restrictive.

Moreover, although specific examples have been illustrated and described herein, it should be appreciated that any subsequent arrangement designed to achieve the same or similar results may be substituted for the specific implementations shown. This disclosure is intended to cover any and all subsequent adaptations or variations of various implementations. Combinations of the above implementations, and other implementations not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single implementation for the purpose of streamlining the disclosure. Examples described above illustrate but do not limit the disclosure. It should also be understood that numerous modifications and variations are possible in accordance with the principles of the present disclosure. As the following claims reflect, the claimed subject matter may be directed to less than all of the features of any of the disclosed examples. Accordingly, the scope of the disclosure is defined by the following claims and their equivalents.

What is claimed is:

1. A test structure (102) comprising:
a frame (110);
a shear reduction plate (130) configured to couple to a first end (212) of a test asset (160); and
multiple rockers (120), each rocker comprising a first end (432) and a second end (434), the first end having a curved contact surface (122) configured to contact the shear reduction plate, the second end having a connector (124) movably coupled to the frame and configured to pivot, responsive to a bending moment (228) applied to the test asset, such that the curved contact surface rocks in contact with the shear reduction plate.

2. The test structure of claim 1, further comprising an axial loader (140) coupled to a second end (214) of the test asset and configured to apply an axial load (220) to the test asset.

3. The test structure of claim 2, further comprising a translational loader (150) coupled to the frame and configured to apply a translational load (222) to the test asset, wherein the translational load is orthogonal to the axial load, and wherein the translational load causes the bending moment applied to the test asset.

4. The test structure of claim 2, wherein the curved contact surface of a particular rocker of the multiple rockers is configured to move to align the axial load along the particular rocker, and wherein the curved contact surface comprises a section of a sphere.

5. The test structure of claim 1, wherein the shear reduction plate is configured to move responsive to rocking of the curved contact surfaces to apply zero shear force and a uniform bending moment on the test asset.

6. The test structure of claim 1, wherein the connector of each rocker comprises a spherical rod eye (428) that includes a spherical bearing (426).

7. The test structure of claim 1, wherein the connector of a particular rocker is movably coupled to a clevis bracket (452) via a clevis pin, wherein the clevis bracket is coupled to the frame.

8. The test structure of claim 1, wherein the connector of a particular rocker is configured to pivot in two orthogonal planes (494, 496), and wherein the curved contact surface of the particular rocker is configured to rock in the two orthogonal planes.

9. The test structure of claim 1, wherein a radius of the curved contact surface of each rocker is proportional to an axial load applied to the test asset.

10. The test structure of claim 1, wherein a distance from a pivot point (126) of the second end to the curved contact surface of a particular rocker is proportional to an axial load to be applied to the test asset, and wherein the pivot point corresponds to a spherical bearing.

11. The test structure of claim 1, wherein the shear reduction plate includes multiple contact plates (132), and wherein the curved contact surface of each rocker is configured to rock in contact with a corresponding contact plate of the multiple contact plates.

12. The test structure of claim 11, wherein the multiple contact plates include a second material with a greater hardness than a first material of the shear reduction plate.

13. A test structure comprising:
a frame (110);
a shear reduction plate (130) configured to couple to a first end (212) of a test asset (160);
multiple rockers (120), each rocker comprising a first end (432) and a second end (434), the first end having a curved contact surface (122) configured to rock in contact with the shear reduction plate, and the second end having a connector (124) movably coupled to the frame, the multiple rockers comprising:
a first set of rockers (412) on a first side (462) of the shear reduction plate; and
a second set of rockers (414) on a second side (464) of the shear reduction plate, each rocker of the second set of rockers aligned, through the shear reduction plate, with a corresponding rocker of the first set of rockers.

14. The test structure of claim 13, further comprising:
the test asset;
an axial loader (140) coupleable to the test asset and configured to apply an axial load (220) to the test asset; and
a translation loader (150) coupleable to the test asset and configured to apply a translation load (222) to the test asset.

15. The test structure of claim 13, wherein the first set of rockers includes four rockers and the second set of rockers includes four rockers, and wherein the connector of each rocker of the multiple rockers is configured to pivot in two orthogonal planes, responsive to a load applied to the test asset, such that the curved contact surface of each rocker rocks in contact with the shear reduction plate.

16. The test structure of claim 13, further comprising one or more springs (528) coupled to the frame and to one or more rockers of the second set rockers, the one or more springs configured to bias the one or more rockers such that a center of the curved contact surfaces is in contact with the shear reduction plate.

17. A method comprising:
applying (602) an axial load to a test asset in a test structure, the test structure comprising:
a frame;
a shear reduction plate coupled to a first end of a test asset; and
multiple rockers, each rocker comprising a first end and a second end, the first end having a curved contact surface configured to contact the shear reduction plate, the second end having a connector movably coupled to the frame and configured to pivot, responsive to a bending moment applied on the test asset, such that the curved contact surface rocks in contact with the shear reduction plate; and
applying (604) a translational load to the test asset, the translational load orthogonal to the axial load, wherein the translational load causes the bending moment.

18. The method of claim 17, wherein application of the axial load and the translational load is associated with a structural failure analysis test.

19. The method of claim 17, wherein the multiple rockers and the shear reduction plate apply a uniform bending moment (228) to the test asset responsive to application of the translational load.

20. The method of claim 19, wherein the multiple rockers and the shear reduction plate apply less than a threshold shear force to the test asset responsive to application of the translational load.

* * * * *